United States Patent
Moros et al.

(10) Patent No.: US 10,463,046 B2
(45) Date of Patent: *Nov. 5, 2019

(54) ANTIMICROBIAL COATINGS CAPABLE OF REDUCING THE NUMBER OF MURINE NOROVIRUS INOCULATED THEREON

(71) Applicant: Allied BioScience, Inc., Dallas, TX (US)

(72) Inventors: Daniel Moros, New York, NY (US); Craig Grossman, Point Roberts, WA (US)

(73) Assignee: Allied Bioscience, Inc., Dallas, TX (US)

( * ) Notice: Subject to any disclaimer, the term of this patent is extended or adjusted under 35 U.S.C. 154(b) by 68 days.

This patent is subject to a terminal disclaimer.

(21) Appl. No.: 15/718,997

(22) Filed: Sep. 28, 2017

(65) Prior Publication Data

US 2018/0014545 A1    Jan. 18, 2018

Related U.S. Application Data

(60) Division of application No. 15/041,974, filed on Feb. 11, 2016, now Pat. No. 9,918,475, which is a continuation-in-part of application No. 14/932,840, filed on Nov. 4, 2015, now Pat. No. 9,856,360.

(60) Provisional application No. 62/114,998, filed on Feb. 11, 2015, provisional application No. 62/075,020, filed on Nov. 4, 2014.

(51) Int. Cl.
| | |
|---|---|
| *C09D 183/00* | (2006.01) |
| *A01N 55/00* | (2006.01) |
| *C09D 183/08* | (2006.01) |
| *A01N 59/16* | (2006.01) |
| *A61L 2/00* | (2006.01) |
| *C09D 5/14* | (2006.01) |
| *A01N 25/02* | (2006.01) |
| *A01N 33/08* | (2006.01) |
| *B05D 1/02* | (2006.01) |
| *B05D 7/14* | (2006.01) |
| *B05D 7/00* | (2006.01) |
| *C09D 179/02* | (2006.01) |
| *C23C 26/00* | (2006.01) |
| *B05D 1/04* | (2006.01) |
| *C08G 77/26* | (2006.01) |
| *C08K 3/22* | (2006.01) |

(52) U.S. Cl.
CPC ............ *A01N 55/00* (2013.01); *A01N 25/02* (2013.01); *A01N 33/08* (2013.01); *A01N 59/16* (2013.01); *A61L 2/00* (2013.01); *B05D 1/02* (2013.01); *B05D 1/04* (2013.01); *B05D 7/14* (2013.01); *B05D 7/544* (2013.01); *C08G 77/26* (2013.01); *C09D 5/14* (2013.01); *C09D 179/02* (2013.01); *C09D 183/08* (2013.01); *C23C 26/00* (2013.01); *C08K 3/22* (2013.01); *C08K 2003/2241* (2013.01); *C09D 183/00* (2013.01)

(58) Field of Classification Search
CPC ..... C09D 183/00; C09D 183/08; C08G 77/26
See application file for complete search history.

(56) References Cited

U.S. PATENT DOCUMENTS

| | | | | |
|---|---|---|---|---|
| 4,048,206 | A | * | 9/1977 | Voronkov ............. A01N 55/00 556/405 |
| 4,740,538 | A | | 4/1988 | Sekutowski |
| 4,865,844 | A | | 9/1989 | Blank |
| 5,945,555 | A | | 8/1999 | Yoshitake |
| 8,951,341 | B2 | | 2/2015 | Jaffrennou |
| 2005/0238839 | A1 | | 10/2005 | Takagi et al. |
| 2009/0317624 | A1 | | 12/2009 | Yoshioka |
| 2010/0234506 | A1 | | 9/2010 | Elizalde |
| 2011/0000539 | A1 | | 1/2011 | Gronet |
| 2013/0040078 | A1 | * | 2/2013 | Scharfe ................ B41M 5/5218 428/32.37 |
| 2013/0167754 | A1 | * | 7/2013 | Wassmer ............... C08G 77/26 106/287.11 |
| 2013/0237409 | A1 | | 9/2013 | Sambandam |
| 2016/0097595 | A1 | | 4/2016 | Ritchey |

FOREIGN PATENT DOCUMENTS

| | | | |
|---|---|---|---|
| DE | 10 2013 208 034 A1 | * | 11/2013 |
| GB | 2 317 178 | * | 3/1998 |
| JP | 47009016 | | 5/1972 |
| JP | 2004204091 | | 1/1997 |

(Continued)

OTHER PUBLICATIONS

English language translation, RU 2450516 (machine generated) (Year: 2012).*

(Continued)

*Primary Examiner* — Margaret G Moore

(74) *Attorney, Agent, or Firm* — Snell & Wilmer L.L.P.

(57) ABSTRACT

The present disclosure provides antimicrobial coatings on a surface comprising a reactive silanol and triethanolamine. In various examples the reactive silane is 3-chloropropylsilane triol. The coating is capable of reducing the number of Murine norovirus and *E. Coli* inoculated on the dried coating. In various examples, the coating further comprises a mixture of peroxotitanium acid and peroxo-modified anatase sol. The compositions may be electrostatically sprayed on the surface, and in certain examples, a mixture of silanol and triethanolamine is spray-coated on the surface followed by an aqueous mixture of peroxotitanium acid and peroxo-modified anatase sol.

16 Claims, 3 Drawing Sheets

(56) References Cited

FOREIGN PATENT DOCUMENTS

| | | |
|---|---|---|
| JP | 2000-351940 | 12/2000 |
| JP | 2003181299 | 7/2003 |
| JP | 2004091697 | 3/2004 |
| JP | 2004204091 | 7/2004 |
| JP | 2004224861 | 8/2004 |
| JP | 2004231887 | 8/2004 |
| JP | 2004337740 | 12/2004 |
| JP | 2005131072 | 5/2005 |
| JP | 2005138059 | 6/2005 |
| JP | 2005199155 | 7/2005 |
| JP | 2005246639 | 9/2005 |
| JP | 2006136758 | 6/2006 |
| JP | 2006136782 | 6/2006 |
| JP | 2006-526686 | 11/2006 |
| JP | 2006337740 | 12/2006 |
| JP | 20108502975 | 8/2007 |
| JP | 2008073588 | 4/2008 |
| JP | 2008188583 | 8/2008 |
| JP | 2008276145 | 11/2008 |
| JP | 2010-111793 | 5/2010 |
| JP | 201126941 | 6/2011 |
| JP | 2013032474 | 2/2013 |
| KR | 1020060045901 A | 5/2006 |
| RU | 2470053 | 12/2012 |
| SU | 346315 | 7/1972 |
| WO | 2007012026 | 1/2007 |
| WO | 2011059101 | 5/2011 |
| WO | 2011099510 | 8/2011 |
| WO | 2012037615 | 3/2012 |
| WO | 2013156327 | 10/2013 |
| WO | 2007097284 | 2/2018 |

OTHER PUBLICATIONS

English language translation abstract, RU 2450516 (machine generated)(Year: 2012).*
Notice of Allowance dated Aug. 22, 2018 in Canadian Application No. 2965978.
Notice of Allowance dated Oct. 11, 2018 in U.S. Appl. No. 15/432,443.
Advisory Action dated Nov. 8, 2018 in U.S. Appl. No. 15/432,428.
Advisory Action dated Nov. 14, 2018 in U.S. Appl. No. 15/432,413.
Non-Final Office Action dated Oct. 29, 2016 in U.S. Appl. No. 15/969,576.
Notice of Allowance dated Aug. 22, 2018 in Japanese Application No. 2017-536331.
Exam Report dated Aug. 30, 2018 in Euporean Application 15857660.3.
Final Office Action dated Aug. 31, 2018 in U.S. Appl. No. 15/432,413.
Final Office Action dated Aug. 31, 2018 in U.S. Appl. No. 15/432,428.
Office Action dated May 29, 2018 in Canadian Application No. 2965978.
Office Action dated May 29, 2018 in Austraiian Application No. 2016219202.
Final Office Action dated Jul. 20, 2018 in U.S. Appl. No. 15/432,443.
Office Actin dated Oct. 10, 2018 in Japanese Application No. 2017-543303.
Final Office Action dated Oct. 18, 2018 in Korean Application No. 10-2017-7014833.
Notice of Allowance dated Nov. 28, 2018 in Korean Application No. 10-2017-7014833.
Notice of Allowance dated Nov. 29, 2018 in U.S. Appl. No. 15/432,413.
Notice of Allowance dated Dec. 26, 2018 in U.S. Appl. No. 15/432,428.
Non-Final Office Action dated Nov. 17, 2017 in U.S. Appl. No. 15/041,971.
Grossman, et al., U.S. Appl. No. 15/969,576, filed May 2, 2018, entitled "Antimicrobial Coatings Comprising Quaternary Silanes".
Examination Report No. 2 dated Mar. 1, 2018 in Australian Application No. 2015343153.
Notice of Acceptance for Patent Application dated May 15, 2018 in Australian Application No. 2015343153.
Notice of Preliminary Rejection dated May 4, 2018 in Korean Application No. 10-2017-7014833.
Notice of Allowance dated Jan. 3, 2018 in U.S. Appl. No. 15/041,974.
Office Action dated Apr. 12, 2018 in Canadian Application No. 2,972,923.
Office Action dated Apr. 25, 2018 in Japanese Patent Application No. 2017-543303.
Office Action dated Jun. 15, 2018 in Russian Application No. 2017124203.
USPTO, Office Action dated Apr. 2, 2018 in U.S. Appl. No. 15/432,443.
USPTO, Office Action dated Apr. 5, 2018 in U.S. Appl. No. 15/432,428.
USPTO, Office Action dated Apr. 16, 2018 in U.S. Appl. No. 15/432,413.
Moros, et al., U.S. Appl. No. 15/432,443, filed Feb. 14, 2017 and entitled "Antimicrobial Coatings Formed by Reaction of Silanes With Triethanolamine to Form Polymeric Siloxanes".
International Preliminary Report on Patentability dated May 9, 2017 in Application No. PCT/US2015/059080.
International Preliminary Report on Patentability dated Aug. 15, 2017 in Application No. PCT/US2016/017599.
Notice of Allowance dated Oct. 24, 2017 in U.S. Appl. No. 14/932,840.
Moros, et al., U.S. Appl. No. 15/720,835, filed Sep. 29, 2017 and entitled "Methods of Coating a Surface With an Antimicrobial Coating Capable of Reducing the Number of Murine Norovirus Inoculated Thereon".
Notice of Allowance dated Sep. 8, 2017 in U.S. Appl. No. 15/432,567.
Examination Report dated Sep. 28, 2017 in Australian Application No. 2015343153.
International Report on Patentability dated Feb. 8, 2019 in PCT Application PCT/US2018/024654.
Office Action dated Mar. 11, 2019 in CA Application 2,965,978.
Office Action dated Mar. 20, 2019 in EP Application 15 857 660.3.
Notice of Allowance dated Feb. 7, 2019 in U.S. Appl. No. 15/969,576.
Non-Final Office Action dated Feb. 11, 2019 in U.S. Appl. No. 15/720,835.

* cited by examiner

ANTIMICROBIAL COATINGS CAPABLE OF REDUCING THE NUMBER OF MURINE NOROVIRUS INOCULATED THEREON

CROSS-REFERENCE TO RELATED APPLICATIONS

This application is a divisional of U.S. Non-Provisional patent application Ser. No. 15/041,974 filed Feb. 11, 2016, which claims benefit of U.S. Provisional Patent Application Ser. No. 62/114,998 filed Feb. 11, 2015 and is a CIP of U.S. Non-Provisional patent application Ser. No. 14/932,840 filed Nov. 4, 2015, which claims benefit of U.S. Provisional Patent Application Ser. No. 62/075,020, filed Nov. 4, 2014, all of which are incorporated herein by reference in their entireties.

FIELD OF THE INVENTION

Embodiments generally relate an anti-microbial coating composition, and a method using that coating composition. In certain embodiments, the coating composition comprises a photocatalyst. In certain embodiments, the photocatalyst comprises a titanyl-oxide moiety. In certain embodiments, the coating composition comprises a silane.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE PREFERRED EMBODIMENTS

Figure 1:
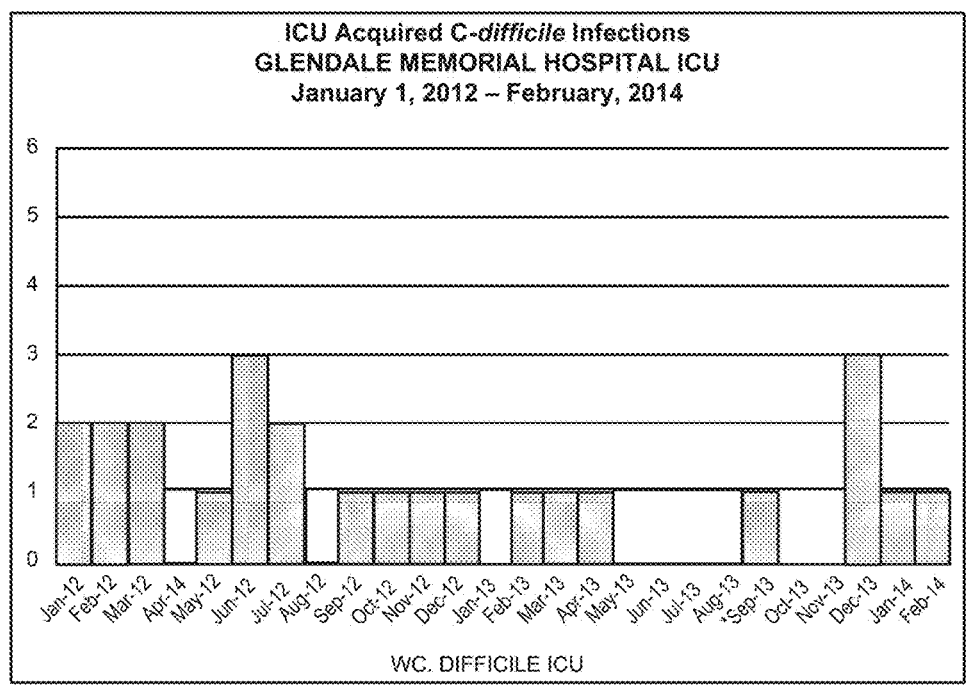
FIG. 1 graphically shows the number of hospital acquired C-difficile infections in the Glendale Memorial Hospital ICU from January 2012 through February 2014.

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In certain embodiments of Inventors' composition and method, a coating is formed on a surface, where that coating comprises a plurality of silicon-oxygen bonds. In certain embodiments of Inventors' composition and method, a coating is formed on a surface, where that coating comprises a plurality of titanium-oxygen bonds in combination with a plurality of silicon-oxygen bonds.

In certain embodiments, a coating comprising a plurality of titanyl-oxide bonds in combination with a plurality of silicon-oxygen bonds is formed by disposing on a surface a silane in combination with one or more compounds comprising one or more titanyl-oxygen bonds. In certain embodiments, a coating comprising a plurality of titanyl-oxide bonds in combination with a plurality of silicon-oxygen bonds is formed by first disposing one or more compounds comprising one or more titanyl-oxygen bonds on the surface, and by disposing a silane onto the surface and over the one or more compounds comprising one or more titanyl-oxygen bonds. In certain embodiments, a coating comprising a plurality of titanyl-oxide bonds in combination with a plurality of silicon-oxygen bonds is formed by simultaneously disposing one or more compounds comprising one or more titanyl-oxygen bonds and a silane onto the surface.

In certain embodiments, Inventors' silane comprises compound 1.

$$\underset{R3}{\overset{R4}{\underset{\diagdown}{\text{Si}}}}\underset{R2}{\overset{\diagup}{\text{—R1}}} \qquad 1$$

In certain embodiments, R1 is selected from the group consisting of OH and O-Alkyl. In certain embodiments, R2 is selected from the group consisting of OH and O-Alkyl. In certain embodiments, R3 is selected from the group consisting of OH and O-Alkyl. In certain embodiments, R4 is selected from the group consisting of OH, O-Alkyl, Alkyl, substituted Alkyl including α-chloro-propyl, α-amino-propyl, and quarternary ammonium salt-substituted Alkyl.

In certain embodiments, Inventors' silane comprises a trihydroxy silane 2.

$$\underset{H\diagdown_O}{\overset{R4}{\underset{\diagdown}{\text{Si}}}}\underset{O\diagdown_H}{\overset{\diagup^H}{O}} \qquad 2$$

In certain embodiments, Inventors' silane comprises a silanetriol 2, wherein R4 is alkyl. In other embodiments, Inventors' silane comprises a silanetriol 2, wherein R4 is alkyl with an amino moiety. In yet other embodiments, Inventors' silane comprises a silanetriol 2, wherein R4 is alkyl with a chlorine substituent. In still other embodiments, Inventors' silane comprises a silanetriol 2, wherein R4 is alkyl with a quarternary ammonium group.

A silsesquioxane is an organosilicon compound 3 where Si represents the element silicon and O represents the element oxygen.

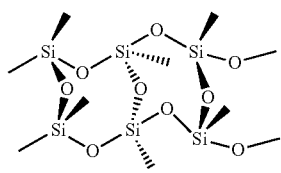

In certain embodiments, after application of Inventors' silane 1 or 2 to either a hard surface, i.e. wall, door, table, and the like, or a soft surface, i.e. bedding, draperies, furniture cushions, and the like, a resulting coating disposed on the hard surface f soft surface comprising a plurality of silsesquioxane structures. In certain embodiments, after application of Inventors' silane 1 or 2 in combination with one or more compounds comprising a titanyl-oxygen moiety, to either a hard surface, i.e. wall, door, table, and the like, or a soft surface, i.e. bedding, draperies, furniture cushions, and the like, a resulting coating disposed on the hard surface/soft surface comprises a plurality of silsesquioxane structures 3 in combination with plurality of titanyl-oxide structures.

Oxidation is a loss of electrons or an increase in oxidation state by a molecule, atom or ion. Substances that have the ability to oxidize other substances are said to be oxidative or oxidizing and are known as oxidizing agents, oxidants, or oxidizers. Put another way, the oxidant removes electrons from another substance, and is thus itself reduced. And, because it "accepts" electrons, it is also called an electron acceptor.

In chemistry, photocatalysis is the acceleration of a photoreaction in the presence of a catalyst. In catalyzed photolysis, light is absorbed by an adsorbed substrate. In photogenerated catalysis, the photocatalytic activity (PCA) depends on the ability of the catalyst to create electron-hole pairs, which generate free radicals (hydroxyl radicals: .OH) able to undergo secondary reactions. Its comprehension has been made possible ever since the discovery of water electrolysis by means of the titanium dioxide.

Certain titanyl-oxide morphologies exhibit photocatalytic characteristics when exposed to Ultra Violet (UV) light. When exposed to UV light, Inventors' Titanyl-Oxide Moieties create electron-hole pairs which generate free radical (e.g., hydroxyl radicals). The degree of photocatalytic strength varies depending on the type of titanyl-oxide, for example anatase titanium oxide (particle size of about 5 to 30 nanometers) is a stronger photocatalyst than rutile titanium oxide (particle size of about 0.5 to 1 microns).

In certain embodiments of Inventors' composition and method, a coating is formed on a surface, where that coating comprises a plurality of titanyl-oxide bonds, where that coating is formed by disposing Inventors' Titanyl-Oxide Moieties onto a target surface.

In certain embodiments of Inventors' composition and method, a coating is formed on a surface, where that coating comprises a plurality of silicon-oxygen bonds, where that coating is formed by disposing Inventors' silane 1 onto the surface.

In certain embodiments of Inventors' composition and method, a coating is formed on a surface, where that coating comprises a plurality of titanyl-oxide bonds, where that coating is formed by disposing on the surface a mixture of Peroxotitanium acid solution and Peroxo-modified anatase sol (collectively "Titanyl-Oxide Moieties").

In certain embodiments, Inventors' Titanyl-Oxide Moieties comprises up to about a total of one weight percent loading of the mixture of Peroxotitanium acid solution and Peroxo-modified anatase sol. In certain embodiments, Inventors' Titanyl-Oxide Moieties comprises about 0.5 weight percent Peroxotitanium acid solution in combination with about 0.5 weight percent Peroxo-modified anatase sol.

Figure 3:
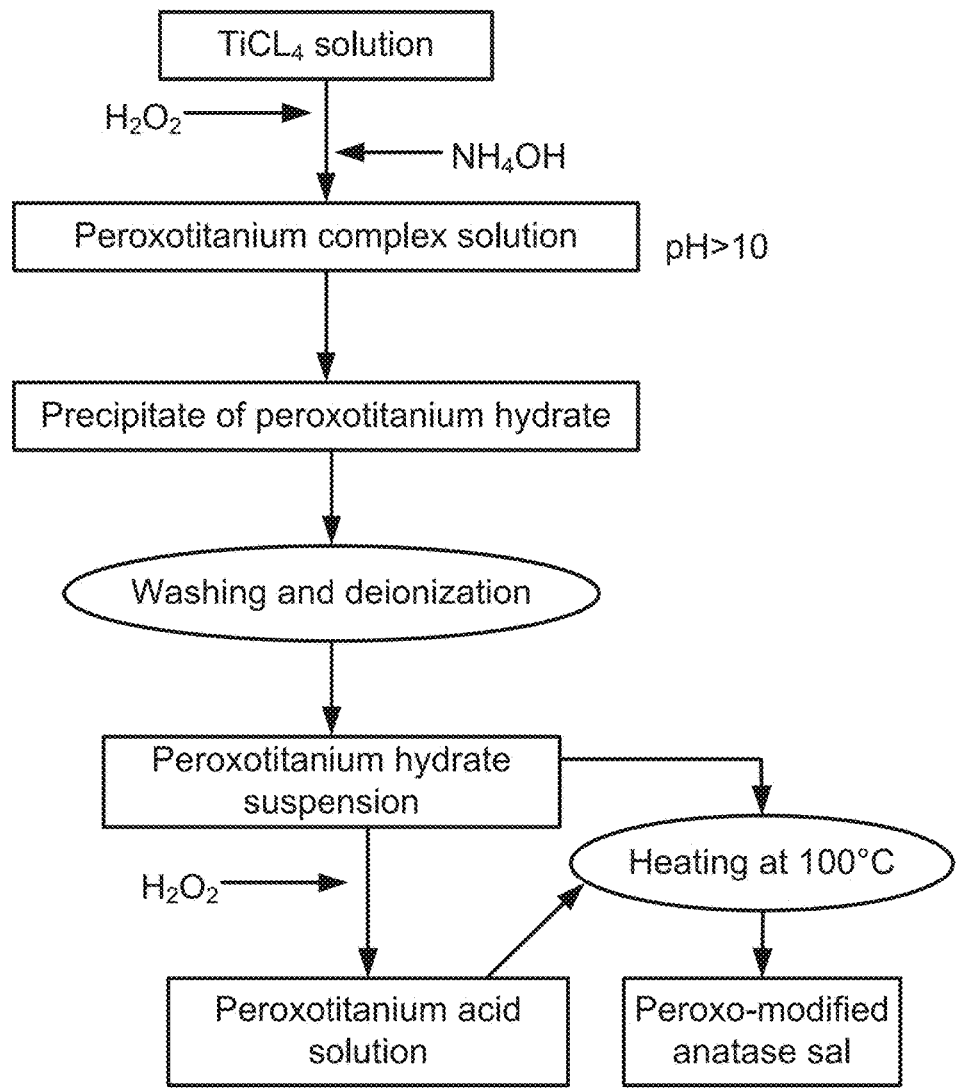
FIG. 3 shows a flowchart of a synthetic procedure for both Peroxotitanium acid solution and Peroxo-modified anatase sol.

A method to prepare both Peroxotitanium acid solution and Peroxo-modified anatase sol is disclosed in Journal of Sol-Gel Science and Technology, September 2001, Volume 22, Issue 1-2, pp 33-40. This publication discloses, inter alfa, the reaction scheme, shown in FIG. 3, which summarizes the synthetic procedure for both Peroxotitanium acid solution and Peroxo-modified anatase sol.

In the following examples, reference is made to coatings ABS-G2015, ABS-G2020, and ABS-G2030. Coating formulation ABS-G2015 comprises a silicone-containing compound having structure V:

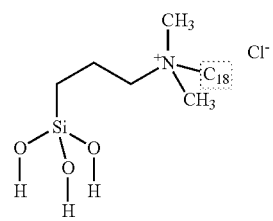

Coating formulation ABS-G2015 further comprises the Titanyl-Oxide Moieties. The order of deposition onto a surface is not critical. In certain embodiments, the silicone-containing compound is first disposed on a surface, and the Titanyl-Oxide Moieties are disposed over that silicone-containing compound. In other embodiments, the Titanyl-Oxide Moieties are first disposed on a surface, and the silicone-containing compound is disposed over that Titanyl-Oxide Moieties-treated surface. In yet other embodiments, the Titanyl-Oxide Moieties and the silicone-containing compound are first pre-mixed, and the resulting mixture is disposed on the surface of the substrate.

Coating formulation ABS-G2020 comprises a silicone-containing compound having structure VI:

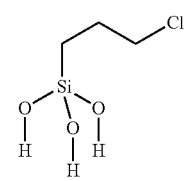

Coating formulation ABS-G2020 further comprises the Titanyl-oxide Moieties. The order of deposition onto a surface is not critical. In certain embodiments, the silicone-containing compound is first disposed on a surface, and the Titanyl-oxide Moieties are disposed over that silicone-containing compound. In other embodiments, the Titanyl-oxide Moieties are first disposed on a surface, and the silicone-containing compound is disposed over that Titanyl-oxide Moieties-treated surface. In yet other embodiments, the Titanyl-oxide Moieties and the silicone-containing compound are first pre-mixed, and the resulting mixture is disposed on the surface of the substrate.

Coating formulation ABS-G2030 comprises a silicone-containing compound having structure VII:

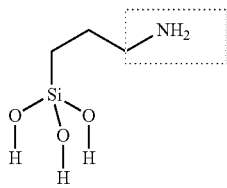

VII

Coating formulation ABS-G2030 further comprises the Titanyl-Oxide Moieties. The order of deposition onto a surface is not critical. In certain embodiments, the silicone-containing compound is first disposed on a surface, and the Titanyl-Oxide Moieties are disposed over that silicone-containing compound. In other embodiments, the Titanyl-Oxide Moieties are first disposed on a surface, and the silicone-containing compound is disposed over that Titanyl-Oxide Moieties-treated surface. In yet other embodiments, the Titanyl-Oxide Moieties and the silicone-containing compound are first pre-mixed, and the resulting mixture is disposed on the surface of the substrate.

The following Examples are presented to further illustrate to persons skilled in the art how to make and use the invention. These Examples are not intended as limitations, however, upon the scope of the invention.

EXAMPLE 1

This Example 1 evaluates the anti-microbial efficacy of coatings ABS-G2015, ABS-G020, and ABS G-2030, against Murine Noro Virus. Murine norovirus (MNV) is a species of norovirus affecting mice. Norovirus is the most common cause of viral gastroenteritis in humans. It affects people of all ages. The virus is transmitted by, inter alia, aerosolization of the virus and subsequent contamination of surfaces. The virus affects around 267 million people and causes over 200,000 deaths each year; these deaths are usually in less developed countries and in the very young, elderly and immunosuppressed.

The test coupons of this Example 1 were prepared using the Procedure recited immediately hereinbelow.

Procedure

Put on sterile gloves.
Prepare the test coupons by wiping them first with Isopropyl Alcohol and allowing to dry.
Clean the test coupons with surface cleaner using a microfiber cloth.
Hold sprayer about eight (8) inches from surface to be cleaned.
Spray on let stand for 1-3 minutes and wipe it off, if the area is extremely dirty allow cleaner to stand longer, or apply a second spray and wipe.
Wipe surface with a clean, damp sponge or cloth.
Allow surface to completely dry.
With gloved hands examine coupons for consistency.
Prepare a 10 volume percent solution of the selected silane in Methanol (MeOH) (10 ml silane in 90 ml MeOH).
Prepare Triethanolamine as a 10 volume percent solution in MeOH.
Combine the triethanolamine solution and the silane solution in a 1:1 ratio on a stir plate at room temperature (ie-100 ml triethanolamine solution added to 100 ml silane solution).

Silane Application

Add the silane triethanolamine solution from to the applicator container.
Fasten the Liquid Hose/Bottle cap assembly tightly on the container.
Connect the air hose from compressor to air fitting on the spray applicator.
Connect the liquid hose to the liquid fitting on the spray applicator.
Plug the power cord into an appropriate receptacle. Turn on the air compressor.
Optimal spraying distance is at least 36 to 48 inches away from the target surface.
Hold the spray gun at right angles to the target surface and spray.
Target surface should just barely glisten with the spray. Do not over-saturate the surface.
Allow target surface to dry, i.e. allow at least 90 weight percent of the methanol liquid carrier to evaporate to give a deposition consisting essentially of the selected silane and triethanolamine. The deposition onto the target surface consists of at least 33 volume percent of the selected silane, at least 33 volume percent of triethanolamine, and up to about 33 volume percent residual methanol carrier liquid.
Rinse spray gun with distilled water prior to applying Inventors' Titanyl-Oxide Moieties (unless using 2 sprayers, one for each product).

Titanyl-Oxide Moieties Application

Add an aqueous mixture of Inventors' Titanyl-Oxide Moieties to the applicator container.
Fasten the Liquid Hose/Bottle cap assembly tightly on the container.
Connect the air hose from compressor to air fitting on the spray applicator.
Connect the liquid hose to the liquid fitting on the spray applicator.
Plug the power cord into an appropriate receptacle. Turn on the air compressor.
Optimal spraying distance is at least 36 to 48 inches away from the target surface.
Hold the spray gun at right angles to the target surface and spray.
Target surface should just barely glisten with the spray. Do not over-saturate the surface.
Allow target surface to dry, i.e. allow at least 90 weight percent of the water liquid carrier to evaporate to give a deposition consisting essentially of Inventors' Titanyl-Oxide Moieties. The deposition onto the target surface consists of at least 66 volume percent of Inventors' Titanyl-Oxide Moieties and up to about 33 volume percent residual water carrier liquid.
Clean the spray gun with distilled water per manufactures' specifications after each day of use.

Tables 2 and 3 recite anti-microbial efficacy data four (4) hours after inoculation of the treated test coupons. Table 2 includes data for ABS-G2020 and ABS-G2030 treated Formica® (paper and melamine resin laminate) coupons. Table 3 includes data for ABS-G2020 and ABS G-2030 treated stain less steel coupons.

TABLE 1

Surface Time-Kill Study Evaluating Four Coating Formulations
Against Murine Norovirus: Time Zero Data

| Test Organism | Contact Time | Sample ID[a] | Viral Counts (TCID$_{50}$ per mL) | Log$_{10}$ Reduction | Percent Reduction |
|---|---|---|---|---|---|
| Murine norovirus | Time Zero | Formica-Ctrl<br>SS-Ctrl | 1.48E+07<br>6.76E+06 | N.A. | |

[a]SS: Stainless Steel

TABLE 2

Surface Time-Kill Study Evaluating Four Coating Formulations Against
Murine Norovirus: 4 Hour Contact Time Data

| Test Organism | Contact Time | Sample ID[a] | Viral Counts (TCID$_{50}$ per mL) | Log$_{10}$ Reduction | Percent Reduction |
|---|---|---|---|---|---|
| Murine norovirus | 4 Hours | Ctrl (Formica)<br>Ctrl (SS)<br>ABS-G2015 (SS)<br>ABS-G2020 (Form)<br>ABS-G2030 (Form) | 1.00E+05<br>6.76E+04<br>6.76E+04<br>≤3.16E+03<br>6.76E+03 | N.A.<br><br>0.00<br>≥1.50<br>1.00 | <br><br>0%<br>≥97%<br>90% |

[a]SS: Stainless Steel; SW: SurfaceWise, Form: Formica
[b]"≤": No viral cytopathology observed beyond toxic levels; therefore titer at or below limit of detection

TABLE 3

Surface Time-Kill Study Evaluating Two Coating Formulations Against *Murine Norovirus*: 4 Hour Contact Time Data

| Test Organism | Contact Time | Sample ID[a] | Viral Counts (TCID$_{50}$ per mL) | Mean Viral Titer | Log$_{10}$ Reduction Relative to Time Zero | Percent Reduction Relative to Time Zero | Log$_{10}$ Reduction Relative to Timed Control | Percent Reduction Relative to Timed Control |
|---|---|---|---|---|---|---|---|---|
| *Murine norovirus* | 4 Hours | SS - Control (Rep A)<br>SS - Control (Rep B)<br>ABS-G2020 (Rep A)<br>ABS-G2020 (Rep B)<br>ABS-G2030 (Rep A)<br>ABS-G2030 (Rep B) | 6.76E+04<br>1.45E+05<br>1.00E+04<br>2.14E+04<br>4.68E+03<br>≤3.16E+03 | 1.06E+05<br><br>1.57E+04<br><br>≤3.92E+03<br> | 1.47<br><br>2.30<br><br>≥2.91<br> | 97%<br><br>99.5%<br><br>≥99.8%<br> | N.A.<br><br>0.83<br><br>≥1.43<br> | <br><br>85.2%<br><br>≥96.3%<br> |

[a]SS: Stainless Steel
[b]"≤": No viral cytopathology observed beyond toxic levels; therefore titer at or below limit of detection

TABLE 4

Surface Time-Kill Study Evaluating Two Coating Formulations Against *Murine Norovirus*: 6 Hour Contact Time Data

| Test Organism | Contact Time | Sample ID[a] | Viral Counts (TCID$_{50}$ per mL) | Mean Viral Titer | Log$_{10}$ Reduction Relative to Time Zero | Percent Reduction Relative to Time Zero | Log$_{10}$ Reduction Relative to Timed Control | Percent Reduction Relative to Timed Control |
|---|---|---|---|---|---|---|---|---|
| *Murine norovirus* | 6 Hours | SS - Control (Rep A)<br>SS - Control (Rep B)<br>ABS-G2020 (Rep A)<br>ABS-G2020 (Rep B)<br>ABS-G2030 (Rep A)<br>ABS-G2030 (Rep B) | 3.16E+04<br>6.76E+04<br>1.00E+04<br>6.76E+03<br>4.68E+03<br>≤3.16E+03 | 4.96E+04<br><br>8.38E+03<br><br>≤3.92E+03<br> | 1.80<br><br>2.58<br><br>≥2.91<br> | 98%<br><br>99.7%<br><br>≥99.8%<br> | N.A.<br><br>0.77<br><br>≥1.10<br> | <br><br>83.1%<br><br>≥92.1%<br> |

[a]SS: Stainless Steel
[b]"≤": No viral cytopathology observed beyond toxic levels; therefore titer at or below limit of detection 1. RAW (mouse macrophage) host cells were prepared in 96-well trays 24 hours prior to use in testing.
2. On the day of testing, a stock vial of test virus, murine norovirus, was removed from storage at −80° C. (titer=5× 10$^8$ TCID50 units per ml). An organic soil load (heat-inactivated fetal bovine serum) was added to obtain a final concentration of 5%.
3. Control (non-coated stainless steel and Formica® (paper and melamine resin laminate)) and coated test carriers [ABS-G2015 (SS); ABS-G2020 (Form Formica® (paper and melamine resin laminate)); ABS-G2030 (Formica® (paper and melamine resin laminate)); ABS-P2015 (SS)] were placed into sterile Petri dishes (one per dish) using pre-sterilized forceps.

4. Viral inocula (0.010 ml) were pipetted onto the center of the control and test carriers, and spread over a surface area of ~1-in$^2$ using a sterile, bent pipette tip.
5. One set of control carriers (per surface material type) was harvested/neutralized immediately to determine Time Zero counts by placement into sterile stomacher bags containing 3 ml of neutralizing solution (calf serum supplemented with 0.001% Na-thiosulfate and 0.001% Na-thioglycollate). The bags were stomached for 120 seconds at high speed to release the viruses from the carriers.
6. The remaining control and test carriers were held under ambient conditions for the duration of each of the specified study contact times of 4 hours and 24 hours [placement distance/configuration: ~68 inches (~1.7 m) below two full-spectrum bulbs, inoculated side facing up towards the lights)]. All carriers were observed to be dried within 10 minutes of inoculation.
7. Upon closure of the respective contact times, the control and test carriers were neutralized by placement into sterile stomacher bags containing 3 ml of neutralizing solution, followed by stomaching as previously described.
8. At the start and finish of each of the contact times, room temperature, relative humidity, and illuminance (lux) were measured and recorded.
9. Control and test carrier eluates were serially diluted (1:10) and plated in replicates of six onto RAW host cells prepared to the appropriate confluency.
10. The plates were observed every 24 to 48 hours to visualize viral cytopathic effects (CPE) and cytotoxicity.
11. Following a 9-day assay incubation period, the plates were formally scored.
12. Log 10 and percent reductions were calculated for each of the test coating formulations relative to the timed control virus counts (per surface type). However, reductions could not be computed for the 24 hour contact time due to insufficient viral recovery from the control carriers.
13. A neutralization validation was performed for each of the test coating formulations (except for ABS-P2015 due to a lack of carriers). One control carrier and one of each test carrier type were placed into stomacher bags containing 3 ml of neutralizer, and processed as previously described. The eluate was serially diluted, and low titer inoculum of the test virus (~3-log 10) was added to each of the dilution tubes per control and test carrier suspension. Aliquots (0.1 ml) of the suspensions were then plated in order to assess cytotoxic levels of the neutralized test materials.

EXAMPLE 2

This Example 2 utilizes the three (3) silanes utilized in coating formulations, namely ABS-G2015, ABS-G2020, and ABS-G2030, but without any Titanyl-Oxide containing compounds. The method of Example 1 from discussed above relating to spray deposition of a silane onto test coupons was utilized in this Example 2. The portion of Example 1 relating to Titanyl-Oxide Moieties Application was not utilized in this Example 2.

TABLE 5

| | | CFU/mL | | | | | | | |
|---|---|---|---|---|---|---|---|---|---|
| | | Untreated | | ABS-G2015E - No TiO2 | | ABS-G2020E - No TiO2 | | ABS-G2030E - No TiO2 | |
| | | A | B | A | B | A | B | A | B |
| 0 hour | 1.E+04 | 1.36E+07 | 9.70E+06 | 5.20E+06 | 1.13E+07 | | | 6.20E+06 | |
| | 1.E+05 | 1.60E+07 | 9.00E+06 | 4.00E+06 | 2.00E+06 | 1.50E+07 | 2.60E+07 | 4.00E+06 | 1.10E+07 |
| 1 hour | 1.E+01 | | | | | 0.00E+00 | 2.00E+03 | 0.00E+00 | 0.00E+00 |
| | 1.E+02 | | | | | 0.00E+00 | 0.00E+00 | 0.00E+00 | 0.00E+00 |
| | 1.E+03 | | | | | 0.00E+00 | 0.00E+00 | 0.00E+00 | 0.00E+00 |
| | 1.E+04 | 1.30E+07 | 9.10E+06 | 1.90E+06 | 2.60E+06 | 0.00E+00 | 0.00E+00 | 0.00E+00 | 0.00E+00 |
| | 1.E+05 | | | | | 0.00E+00 | 0.00E+00 | 0.00E+00 | 0.00E+00 |
| 4 hour | 1.E+01 | | | 1.00E+02 | 3.00E+02 | 0.00E+00 | 1.00E+02 | 0.00E+00 | 0.00E+00 |
| | 1.E+02 | | | | 1.50E+04 | 0.00E+00 | 0.00E+00 | 0.00E+00 | 0.00E+00 |
| | 1.E+03 | | | | | 0.00E+00 | 0.00E+00 | 0.00E+00 | 0.00E+00 |
| | 1.E+04 | 3.70E+06 | 3.40E+06 | | | 0.00E+00 | 0.00E+00 | 0.00E+00 | 0.00E+00 |
| | 1.E+05 | | | | | 0.00E+00 | 0.00E+00 | 0.00E+00 | 0.00E+00 |

TABLE 6

| | Log Reduction from Time Zero | | | |
|---|---|---|---|---|
| | Control | ABS-G2015E | ABS-G2020E | ABS-G2030E |
| 0 hour | N/A | 0.25 | 0.40 | 0.49 |
| 1 hour | 1.14 | 1.29 | 5.33 | 7.81 |
| 4 hour | 1.16 | 2.91 | 6.71 | 7.81 |

TABLE 7

| Percent Reduction | | | |
|---|---|---|---|
| | ABS-G2015H | ABS-G2020H | ABS-G2030H |
| 0 hour | 53.42% | −69.77% | 41.48% |
| 1 hour | 79.64% | 100.00% | 100.00% |
| 4 hour | 99.86% | 100.00% | 100.00% |

TABLE 5 recites CFU/mL data for each of the three coating formulations, wherein each formulation did not include one or more titanium-oxide moieties. TABLE 6 recites Log Reduction data for the three formulations evaluated, wherein each formulation did not include one or more titanium-oxide moieties. TABLE 7 recites Percent Reduction data for the three formulations utilized, wherein each formulation did not include one or more titanium-oxide moieties.

EXAMPLE 3

This Example 3 utilizes complete formulations ABS-G2015, AB-G2020, and ABS-G2030, where those coating formulations were disposed on stainless steel test coupons using the full procedure of Example 1. In one set of experiments, the formulations were disposed onto the test coupons using an electrostatic spray assembly. In another set of experiments, the formulations were disposed onto the test coupons using a non-electrostatic spray assembly.

Tables 8, 9, and 10, recite anti-microbial efficacy data for the electrostatic spray embodiments. Tables 11, 12, and 13, recite anti-microbial efficacy data for the non-electrostatic spray embodiments.

TABLE 8

| | | CFU/mL | | | | | | | |
|---|---|---|---|---|---|---|---|---|---|
| | | Untreated | | ABS-G2015E | | ABS-G2020E | | ABS-G2030E | |
| | | A | B | A | B | A | B | A | B |
| 0 hour | 1.E+04 | 3.08E+07 | 4.80E+06 | | | 2.58E+07 | 1.66E+07 | | |
| | 1.E+05 | 1.97E+08 | 2.30E+07 | 3.10E+07 | 4.10E+07 | 2.60E+07 | 3.40E+07 | 2.10E+07 | 2.00E+07 |
| 1 hour | 1.E+01 | | | | | 8.00E+02 | 6.00E+02 | 0.00E+00 | 0.00E+00 |
| | 1.E+02 | | | | | 1.00E+03 | 0.00E+00 | 0.00E+00 | 0.00E+00 |
| | 1.E+03 | | | | | 0.00E+00 | 0.00E+00 | 0.00E+00 | 0.00E+00 |
| | 1.E+04 | 2.90E+06 | 6.40E+06 | 2.70E+06 | 3.80E+06 | 0.00E+00 | 0.00E+00 | 0.00E+00 | 0.00E+00 |
| 4 hour | 1.E+01 | | | 1.63E+04 | | 1.00E+02 | 0.00E+00 | 0.00E+00 | 0.00E+00 |
| | 1.E+02 | | | 2.70E+04 | 6.20E+04 | 0.00E+00 | 0.00E+00 | 0.00E+00 | 0.00E+00 |
| | 1.E+03 | 2.70E+06 | 1.90E+05 | 7.00E+04 | 8.00E+04 | 0.00E+00 | 0.00E+00 | 0.00E+00 | 0.00E+00 |
| | 1.E+04 | 1.30E+07 | 1.70E+06 | 2.00E+05 | 1.00E+05 | 0.00E+00 | 0.00E+00 | 0.00E+00 | 0.00E+00 |

TABLE 9

| Log Reduction from Time Zero | | | | |
|---|---|---|---|---|
| | Control | ABS-G2015E | ABS-G2020E | ABS-G2030E |
| 0 hour | N/A | 0.25 | 0.40 | 0.49 |
| 1 hour | 1.14 | 1.29 | 5.33 | 7.81 |
| 4 hour | 1.16 | 2.91 | 6.71 | 7.81 |

TABLE 10

| Percent Reduction from Time Zero | | | | |
|---|---|---|---|---|
| | Control | ABS-G2015E | ABS-G2020E | ABS-G2030E |
| 0 hour | N/A | 43.66% | 59.94% | 67.92% |
| 1 hour | 92.72% | 94.91% | 99.9995% | 99.999998% |
| 4 hour | 93.12% | 99.88% | 99.99998% | 99.999998% |

TABLE 11

| | | CFU/mL | | | | | | | |
|---|---|---|---|---|---|---|---|---|---|
| | | Untreated | | ABS-G2015H | | ABS-G2020H | | ABS-G2030H | |
| | | A | B | A | B | A | B | A | B |
| 0 hour | 1.E+04 | 6.00E+05 | 4.00E+05 | 5.00E+05 | 4.00E+05 | 1.00E+06 | 8.00E+05 | 1.00E+05 | 1.00E+05 |
| | 1.E+05 | 2.00E+06 | 2.00E+06 | 0.00E+00 | 0.00E+00 | 0.00E+00 | 1.00E+06 | 0.00E+00 | 0.00E+00 |
| 1 hour | 1.E+01 | | | | | | | | |
| | 1.E+02 | | | | | | | | |
| | 1.E+03 | 9.00E+05 | 1.58E+06 | 9.10E+05 | 6.70E+05 | 2.00E+05 | 5.70E+05 | 0.00E+00 | 0.00E+00 |
| | 1.E+04 | 1.40E+06 | 1.70E+06 | 1.20E+06 | 3.00E+05 | 2.00E+05 | 9.00E+05 | 0.00E+00 | 0.00E+00 |
| | 1.E+05 | 0.00E+00 | 0.00E+00 | 4.00E+06 | 0.00E+00 | 0.00E+00 | 0.00E+00 | 0.00E+00 | 0.00E+00 |

TABLE 11-continued

| | CFU/mL | | | | | | | |
|---|---|---|---|---|---|---|---|---|
| | Untreated | | ABS-G2015H | | ABS-G2020H | | ABS-G2030H | |
| | A | B | A | B | A | B | A | B |
| 4 hour 1.E+01 | | | | | | | | |
| 1.E+02 | | | | | | | | |
| 1.E+03 | 1.28E+06 | 4.80E+05 | 1.00E+04 | 4.00E+04 | 0.00E+00 | 0.00E+00 | 0.00E+00 | 0.00E+00 |
| 1.E+04 | 8.00E+05 | 4.00E+05 | 0.00E+00 | 0.00E+00 | 0.00E+00 | 0.00E+00 | 0.00E+00 | 0.00E+00 |
| 1.E+05 | 1.00E+06 | 1.00E+06 | 0.00E+00 | 0.00E+00 | 0.00E+00 | 0.00E+00 | 0.00E+00 | 0.00E+00 |

TABLE 12

| | Log Reduction | | |
|---|---|---|---|
| | ABS-G2015H | ABS-G2020H | ABS-G2030H |
| 0 hour | 0.74 | 0.25 | 1.40 |
| 1 hour | −0.10 | 0.47 | 5.97 |
| 4 hour | 2.00 | 5.92 | 5.92 |

TABLE 13

| | Percent Reduction | | |
|---|---|---|---|
| | ABS-G2015H | ABS-G2020H | ABS-G2030H |
| 0 hour | 82.00% | 44.00% | 96.00% |
| 1 hour | −26.88% | 66.49% | 100.00% |
| 4 hour | 98.99% | 100.00% | 100.00% |

EXAMPLE 4

A study was conducted at the Glendale Memorial Hospital and Health Center in Glendale, Calif. (the "Glendale Memorial Hospital Study"). The Center has a 24 bed intensive care (ICU). The study was performed between May 10 and Sep. 30, 2013. The Glendale Memorial Hospital Study was designed to assess the anti-microbial efficacy of coating composition ABS-G2015, described hereinabove, where that coating composition was applied using the complete method of Example 1 herein.

In the Glendale Memorial Hospital Study, the entire ICU was subjected to the two step spray regime described herein to treat all surfaces in each room including hard surfaces (beds, tray tables, bed rail, walls, etc.) and soft surfaces (drapes, cloth and vinyl covered chairs, etc.). More specifically, each surface was first electrostatically spray coated at room temperature using an aqueous composition formed by mixing Octadecylaminodimethyltrihydroxysilylpropyl Ammonium Chloride (the "Silylated Quarternary Amine") at about 3.6 weight percent in water.

After about fifteen (15) minutes after the electrostatic spray coating using the aqueous Silylated Quarternary Amine, each surface was then electrostatically coated at room temperature using the Titanyl-Oxide Moieties described hereinabove.

The treated surfaces were maintained at room temperature during the spray deposition of the aqueous Silylated Quarternary Amine, and during the spray deposition of the Titanyl-Oxide Moieties. None of the treated surfaces were subjected to any elevated heat treatment wherein the treated surface was heated to a temperature greater than about room temperature after completion of the two step coating regime.

Ninety-five (95) specific sites in the ICU were selected for recurring sampling at weeks 1, 2, 4, 8, and 15, after the two step spraying regime. Those selected sites included bed rails, bed controls, tray tables, and walls above sinks. Samples were also collected from the two ICU nursing stations and waiting lobby including countertops, phones, computer keyboards, chair armrests and end tables. All movable items were inconspicuously tagged and coded over the course of the study so that the same objects could be sampled.

Areas of 100 $cm^2$ were sampled using a sponge stick containing Letheen broth (3M, St. Paul, Minn.) to neutralize any residual disinfectant. After collection the samples were immediately placed on ice packs and sent overnight to the University of Arizona for analysis by Professor Charles Gerba.

FIG. 1 hereto is a true and accurate copy of a first graph provided by the Manager, Infection Prevention, Dignity Health/Glendale Memorial Hospital & Health Center. Exhibit 1 graphically shows the number of hospital acquired C-difficile infections in the Glendale Memorial Hospital ICU from January 2012 through February 2014.

FIG. 1 indicates that with the exception of September 2013, there were no hospital acquired C-difficile infections originating in the ICU during the period May 2013 through November 2013. Thus, FIG. 1 shows that there was a single hospital acquired C-difficile infection originating in the ICU during the six month period May 2013 through November 2013.

FIG. 1 further shows that, other than the six month period May 2013 through November 2013, there was no other 6 month period during the 25 months from January 2012 through February 2014 wherein only a single hospital acquired C-difficile infection originated in the ICU.

Figure 2:
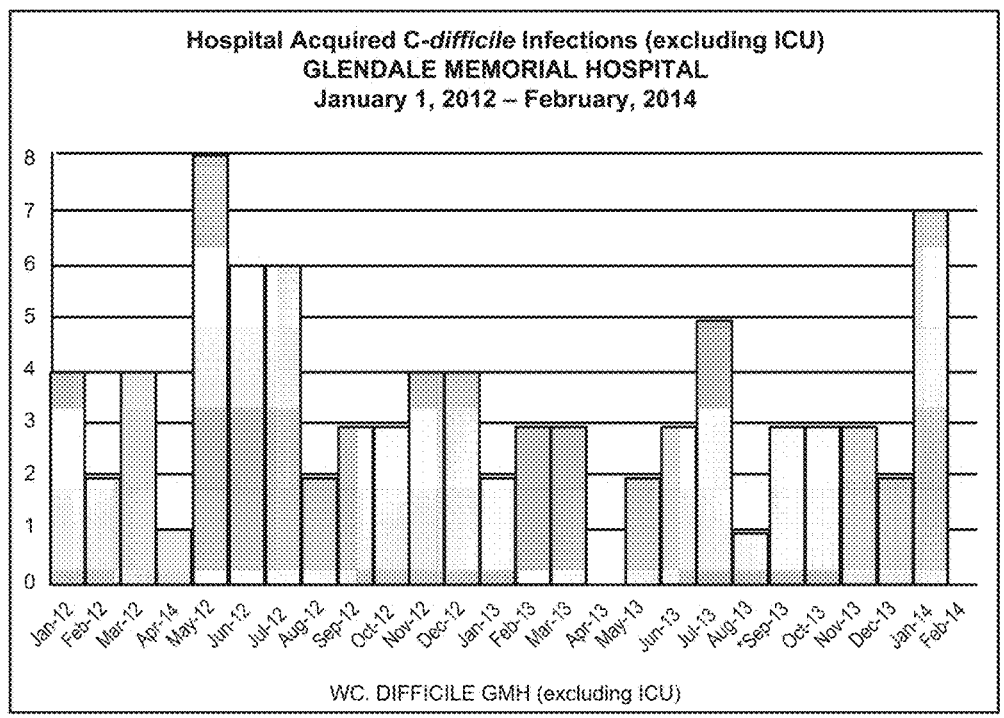
FIG. 2 graphically shows the number of hospital acquired C-difficile infections at the Glendale Memorial Hospital (excluding ICU) from January 2012 through February 2014.

All surfaces in the ICU were treated as described hereinabove during the first week of May 2013 as part of the Glendale Memorial Hospital Study. FIG. 2 hereto is a true and accurate copy of a second graph provided by the Manager, Infection Prevention, Dignity Health/Glendale Memorial Hospital & Health Center. Exhibit 2 graphically shows the number of hospital acquired C-difficile infections at the Glendale Memorial Hospital (excluding ICU) from January 2012 through February 2014.

FIG. 2 indicates that, with the exception of April 2013, there were between 1 and 8 hospital acquired C-difficile infections every month during the 25 month period in hospital areas outside of the ICU. During the period May 2013 through November 2013, FIG. 2 shows that there were a total of 20 hospital acquired C-difficile infections originating outside of the ICU at the Glendale Memorial Hospital.

FIGS. 1 and 2 show that during the period May 2013 through November 2013, a single hospital acquired C-difficile infection originated in the ICU at the Glendale Memorial Hospital, and a total of 20 hospital acquired C-difficile infections originated outside of the ICU at the Glendale Memorial Hospital.

Clostridium difficile colitis or pseudomembranous colitis is colitis (inflammation of the large intestine) resulting from infection with Clostridium difficile, a type of spore-forming bacteria. It causes an infectious diarrhea called C. difficile diarrhea. Latent symptoms of Clostridium difficile infection (CDI) often mimic some flu-like symptoms and may mimic disease flare-ups in people with inflammatory bowel disease-associated colitis. C. difficile releases toxins that may cause bloating and diarrhea, with abdominal pain, which may become severe.

C. difficile is transmitted from person to person by the fecal-oral route. The organism forms heat-resistant spores that are not killed by alcohol-based hand cleansers or routine surface cleaning. Thus, these spores survive in clinical environments for long periods. Because of this, the bacteria may be cultured from almost any surface.

Clostridium difficile spores are extremely hardy, and can survive for long amounts of time in environments devoid of food. The spores are resistant to drying and heating, and also have resistance to many forms of antiseptic cleaners. C. diff can also survive in spore form for as long as five months. The ability of C. diff to survive in this resistant form poses quite a challenge for hospitals.

Because C. diff forms heat-resistant spores that are not killed by alcohol-based hand cleansers or routine surface cleaning, the data of FIGS. 1 and 2 demonstrate that treatment of hard surfaces and soft surface in the Glendale Memorial Hospital ICU with ABS-G2015 necessarily reduced the occurrence of C. diff spores in that ICU. The data of FIG. 2 show that other hospital departments that were not treated with ABS-G2015 coating composition experienced a much greater level of hospital acquired C. diff infections, thereby corroborating the anti-microbial efficacy of the coating resulting from application of ABS-G2015 against C. diff spores.

In coating formulations ABS G2015, G2020, and G2030, depending on the stoichiometry of the mixture of triethanolamine and the organosilane, one or polymeric species are formed on a treated surface. In certain embodiments, and as shown in Reaction Scheme 2, triethanolamine 9 and organosilane 1 react to form a linear polymer 10, wherein n is greater than or equal to 1 and less than or equal to about 10.

REACTION SCHEME 2

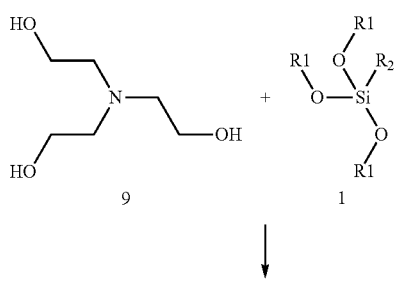

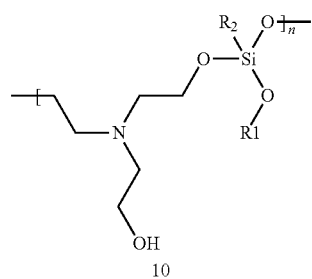

In other embodiments, and as shown in Reaction Scheme 3, triethanolamine 9 and organosilane 1 react to form a branched polymer 11.

REACTION SCHEME 3

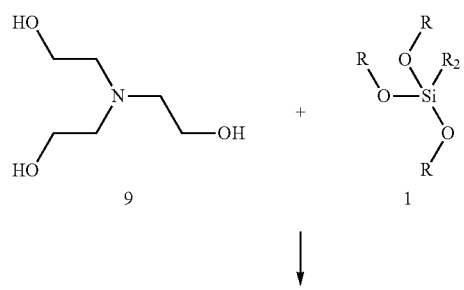

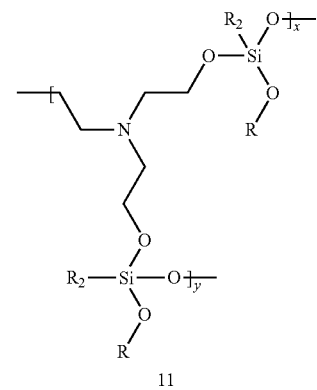

wherein in Reaction Scheme 3, x is greater than or equal to 1 and less than or equal to about 10, and wherein y is greater than or equal to 1 and less than or equal to about 10.

In other embodiments, and as shown in Reaction Scheme 4, triethanolamine 9 and organosilane 1 react to form a cross-linked polymer 12.

REACTION SCHEME 4

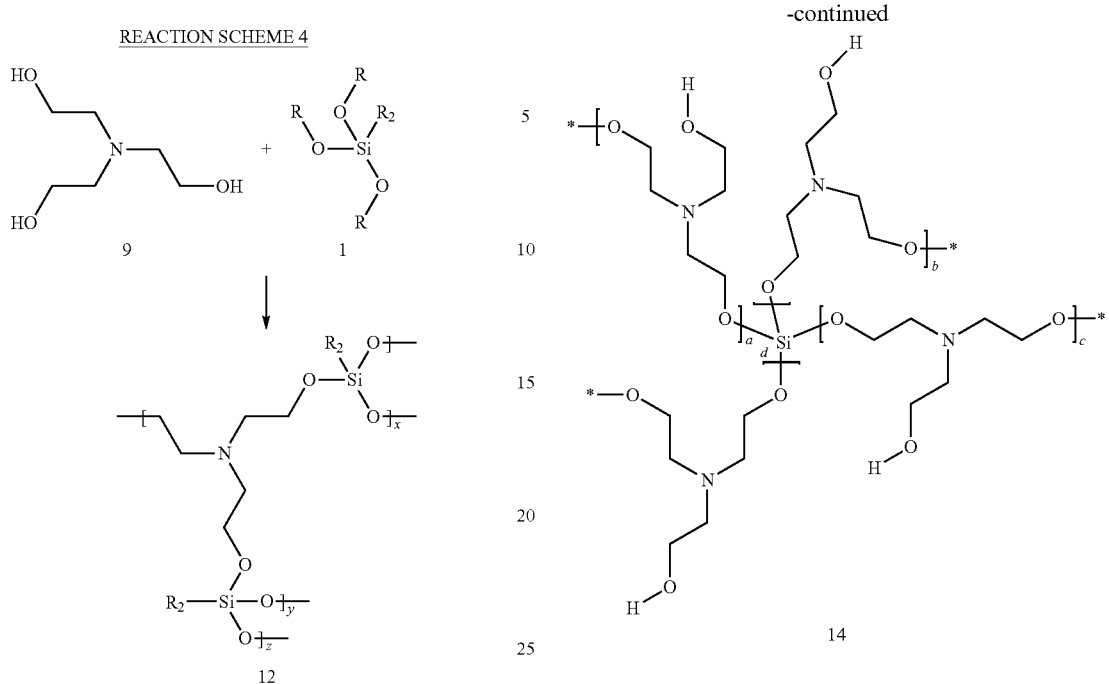

wherein in Reaction Scheme 4, x is greater than or equal to 1 and less than or equal to about 10, and wherein y is greater than or equal to 1 and less than or equal to about 10, and wherein z is greater than or equal to 1 and less than or equal to about 10.

In certain embodiments, Inventors' organosilane comprises tetraethylorthosilicate 13. In certain embodiments and as shown in Reaction Scheme 5 and depending on the stoichiometry of the starting materials 9 and 13, Inventors' cross-linked polymeric material 14 is formed by reaction of tetraethylorthosilicate 13 and triethanolamine 9. Reaction Scheme 5 illustrates a single Si atom having four (4) different polymer chains originating therefrom. Those skilled in the art will appreciate that Inventors' cross-linked polymer material 14 comprises a very high cross-link density.

wherein in Reaction Scheme 5, a is greater than or equal to 1 and less than or equal to about 10, and wherein b is greater than or equal to 1 and less than or equal to about 10, and wherein c is greater than or equal to 1 and less than or equal to about 10, and wherein d is greater than or equal to 1 and less than or equal to about 10.

In certain embodiments and as shown in Reaction Scheme 6 and depending on the stoichiometry of the starting materials 15 and 13, Inventors' cross-linked polymeric material 16 is formed by reaction of tetraethylorthosilicate 13 and diethanolamine 13. Reaction Scheme 6 illustrates a single Si atom having four (4) different polymer chains originating therefrom. Those skilled in the art will appreciate that Inventors' cross-linked polymer material 16 comprises a very high cross-link density.

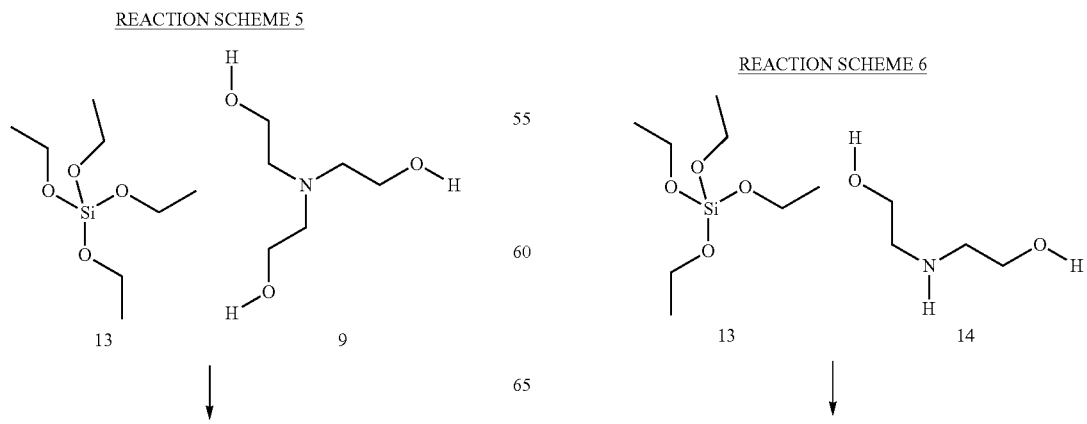

-continued

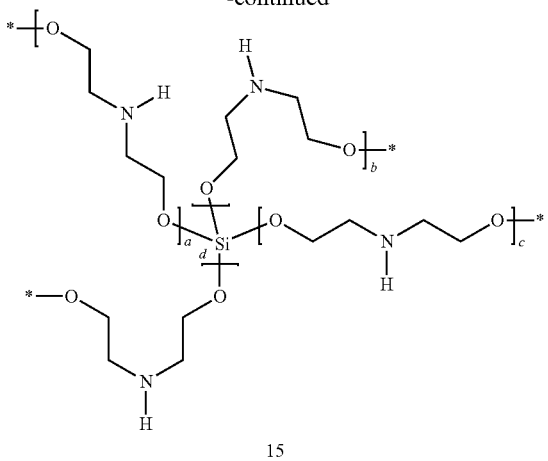

15 wherein in Reaction Scheme 6, a is greater than or equal to 1 and less than or equal to about 10, and wherein b is greater than or equal to 1 and less than or equal to about 10, and wherein c is greater than or equal to 1 and less than or equal to about 10, and wherein d is greater than or equal to 1 and less than or equal to about 10.

While the preferred embodiments of the present invention have been illustrated in detail, it should be apparent that modifications and adaptations to those embodiments may occur to one skilled in the art without departing from the scope of the present invention.

We claim:

1. An antimicrobial coating on a surface of a substrate, the coating comprising triethanolamine, a mixture of peroxotitanium acid and peroxo-modified anatase sol, and a silane having structure VI:

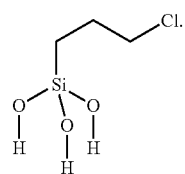

2. The antimicrobial coating of claim 1, wherein the substrate is paper and melamine resin laminate.

3. The antimicrobial coating of claim 2, wherein the antimicrobial coating exhibits ≥1.50 log viral count reduction in Murine norovirus 4 hours after initial inoculation of the coating with Murine norovirus.

4. The antimicrobial coating of claim 1, wherein the substrate is stainless steel.

5. The antimicrobial coating of claim 4, wherein the antimicrobial coating exhibits about a 2.3 log viral count reduction in Murine norovirus 4 hours after initial inoculation of the coating with Murine norovirus.

6. The antimicrobial coating of claim 4, wherein the antimicrobial coating exhibits about a 2.58 log viral count reduction in Murine norovirus 6 hours after initial inoculation of the coating with Murine norovirus.

7. A method of coating a surface of a substrate with the antimicrobial coating of claim 1, which method comprises:
   (a) spray-coating on the surface a methanolic composition comprising triethanolamine and a silane having structure VI:

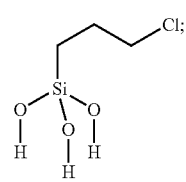

(b) allowing the methanolic composition to dry;
   (c) spray-coating on the surface an aqueous composition of peroxotitanium acid and peroxo-modified anatase sol; and
   (d) allowing the aqueous composition to dry, forming the antimicrobial coating.

8. The method of claim 7, wherein the substrate is stainless steel.

9. The method of claim 8, wherein the spray-coating of both the methanolic composition and the aqueous composition comprise electrostatic spraying.

10. The method of claim 9, wherein the antimicrobial coating exhibits about a 5.33 log reduction in *E. Coli* 1 hour after initial inoculation of the coating with *E. Coli*.

11. The method of claim 9, wherein the antimicrobial coating exhibits about a 6.71 log reduction in *E. Coli* 4 hours after initial inoculation of the coating with *E. Coli*.

12. The method of claim 8, wherein neither the spray-coating of the methanolic composition nor the spray-coating of the aqueous composition comprises electrostatic spraying.

13. The method of claim 12, wherein the antimicrobial coating exhibits about a 0.47 log reduction in *E. Coli* 1 hour after initial inoculation of the coating with *E. Coli*.

14. The method of claim 12, wherein the antimicrobial coating exhibits about a 5.92 log reduction in *E. Coli* 4 hours after initial inoculation of the coating with *E. Coli*.

15. The method of claim 7, wherein allowing the methanolic composition to dry comprises allowing at least 90 weight percent of the methanol to evaporate from the surface.

16. The method of claim 7, wherein allowing the aqueous composition to dry comprises allowing at least 90 weight percent of the water to evaporate from the surface.

* * * * *